(12) United States Patent
Scott

(10) Patent No.: US 8,800,564 B2
(45) Date of Patent: Aug. 12, 2014

(54) TRACHEOSTOMY APPLIANCES AND METHODS FOR THE TREATMENT OF SLEEP APNEA SYNDROMES

(75) Inventor: S. David Scott, Erdenheim, PA (US)

(73) Assignee: Elaine D. Scott, Manheim, PA (US)

( * ) Notice: Subject to any disclaimer, the term of this patent is extended or adjusted under 35 U.S.C. 154(b) by 1727 days.

(21) Appl. No.: 11/869,387

(22) Filed: Oct. 9, 2007

(65) Prior Publication Data

US 2008/0072912 A1 Mar. 27, 2008

Related U.S. Application Data

(63) Continuation-in-part of application No. 11/368,993, filed on Mar. 6, 2006, now abandoned.

(60) Provisional application No. 60/659,771, filed on Mar. 9, 2005.

(51) Int. Cl.
*A61M 11/00* (2006.01)

(52) U.S. Cl.
USPC ............. 128/207.14; 128/207.15; 128/207.16

(58) Field of Classification Search
USPC .................. 128/848, 200.24, 200.26, 205.24, 128/207.14, 207.15, 207.16, 207.29
See application file for complete search history.

(56) References Cited

U.S. PATENT DOCUMENTS

| | | | |
|---|---|---|---|
| 1,592,471 A | 7/1926 | Smolensky | |
| 3,137,299 A | 6/1964 | Tabor | |
| 3,263,684 A | 8/1966 | Bolton | |
| 4,488,545 A * | 12/1984 | Shen | 128/207.29 |
| 4,538,607 A | 9/1985 | Saul | |
| 4,582,058 A | 4/1986 | Depel et al. | |
| 4,759,356 A | 7/1988 | Muir | |
| 4,815,472 A * | 3/1989 | Wise et al. | 600/488 |
| 4,877,025 A | 10/1989 | Hanson | |
| 5,031,613 A * | 7/1991 | Smith et al. | 128/207.14 |
| 5,048,518 A | 9/1991 | Eliachar et al. | |
| 5,259,378 A | 11/1993 | Huchon et al. | |
| 5,367,292 A * | 11/1994 | Szoke et al. | 340/608 |
| 5,392,775 A | 2/1995 | Adkins, Jr. et al. | |
| 5,464,011 A | 11/1995 | Bridge | |
| 5,487,382 A | 1/1996 | Bezicot | |
| 5,505,198 A | 4/1996 | Siebens et al. | |
| 5,840,091 A * | 11/1998 | Strong | 55/385.1 |
| 5,954,050 A * | 9/1999 | Christopher | 128/204.23 |
| 6,189,534 B1 | 2/2001 | Zowtiak et al. | |
| 6,193,751 B1 | 2/2001 | Singer | |
| 6,439,233 B1 * | 8/2002 | Geertsema | 128/207.16 |
| 6,454,724 B1 | 9/2002 | Greene | |
| 6,502,572 B1 * | 1/2003 | Berthon-Jones et al. | 128/204.23 |
| 6,588,428 B2 | 7/2003 | Shikani et al. | |
| 6,668,831 B1 * | 12/2003 | Hegwood | 128/207.14 |

(Continued)

OTHER PUBLICATIONS

Olympic Medical, Olympic Trach-Button, 4 page pamphlet, (date unknown) (admitted prior art).

(Continued)

*Primary Examiner* — Steven Douglas
(74) *Attorney, Agent, or Firm* — Howson & Howson LLP

(57) ABSTRACT

Small tracheostomy appliances for use in treating Sleep Apnea Syndrome. The appliances are inserted in a tracheotomy incision, low on a patient's neck to equalize intratracheal pressure with ambient pressure under certain conditions to prevent undesirable increases in blood $CO_2$ that could otherwise cause arousals from sleep.

15 Claims, 9 Drawing Sheets

(56) References Cited

U.S. PATENT DOCUMENTS

| | | | |
|---|---|---|---|
| 6,990,980 B2 | 1/2006 | Richey, II | |
| 7,021,314 B1 * | 4/2006 | Lane | 128/207.29 |
| 2004/0123868 A1 | 7/2004 | Rutter | |
| 2005/0171432 A1 | 8/2005 | Crutchrield et al. | |

OTHER PUBLICATIONS

Farney et al., "Transtracheal Oxygen, Nasal CPAP and Nasal Oxygen in Five Patients with Obstructive Sleep Apnea", American College of Chest Physicians, vol. 101, issue No. 5, pp. 1228-1235, May 1992.

Chauncey et al., "Preliminary Findings in the Treatment of Obstructive Sleep Apnea with Transtracheal Oxygen", Sleep, vol. 13, Issue No. 2, pp. 167-174, Association of Professional Sleep Societies, Raven Press, Ltd., New York, Feb. 1990.

McGinley et al., "A Nasal Cannula Can Be Used to Treat Obstructive Sleep Apnea", American Journal of Respiratory Critical Care Medicine, vol. 176, pp. 194-200, Mar. 15, 2007.

Sleep Disorder Solutions, Inc., What is sleep apnea? date unknown, 12 pages, www.sleepdisordersolutions.net.

* cited by examiner

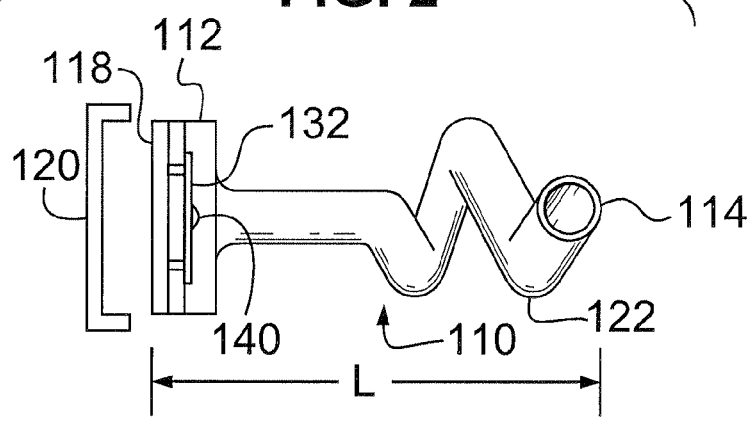
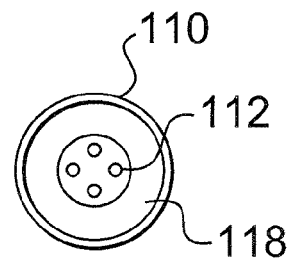
FIG. 3
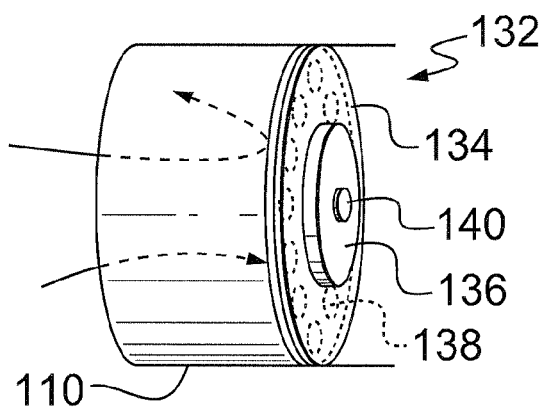
FIG. 4A
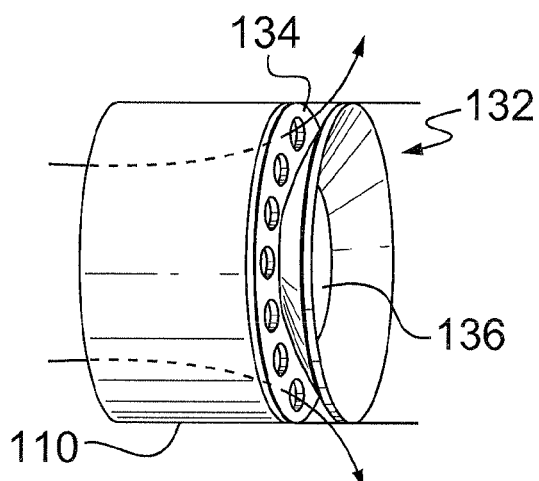
FIG. 4B

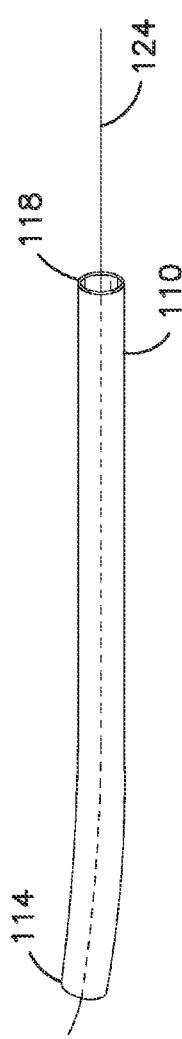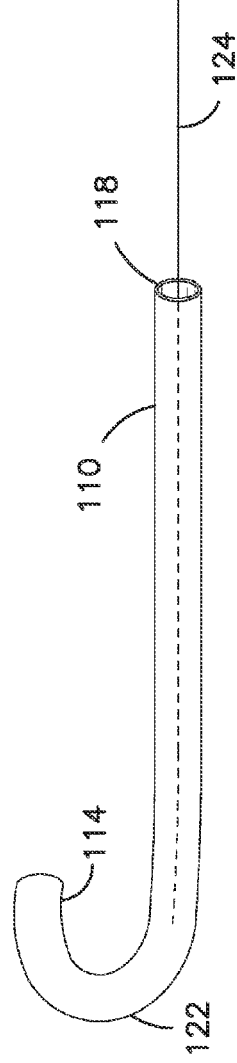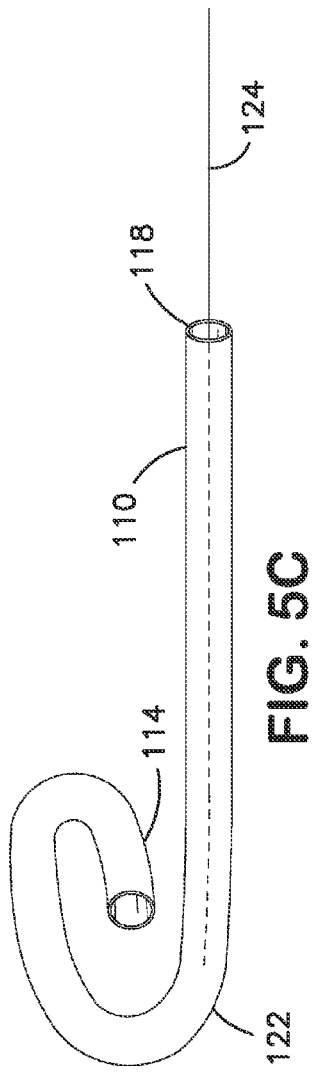

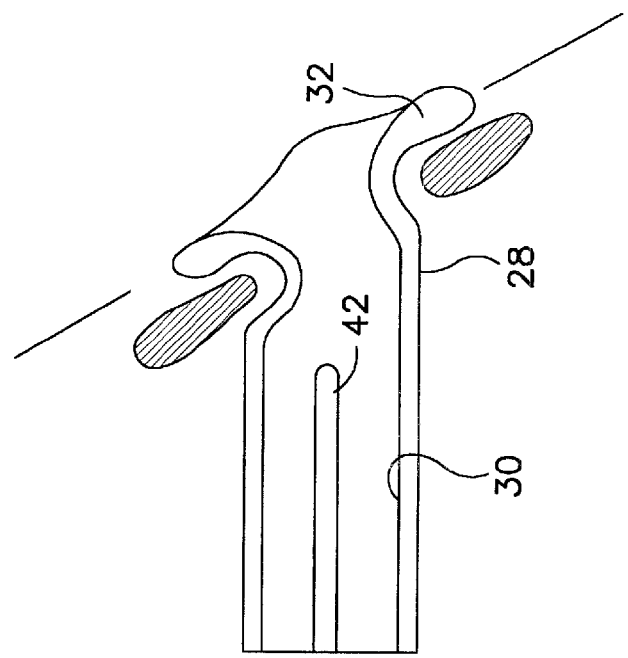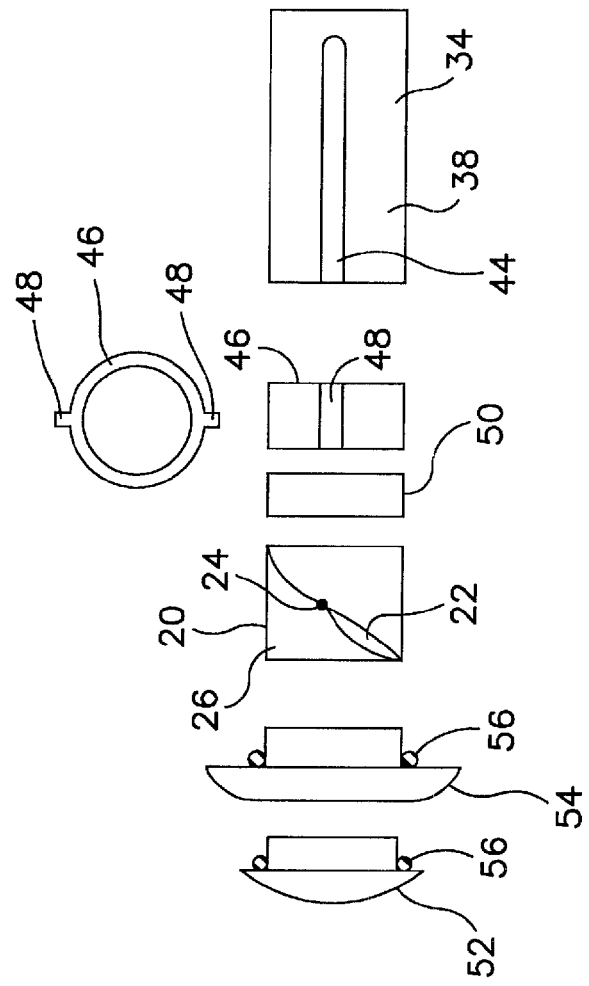
FIG. 9

TRACHEOSTOMY APPLIANCES AND METHODS FOR THE TREATMENT OF SLEEP APNEA SYNDROMES

CROSS-REFERENCE TO RELATED APPLICATIONS

This application is a continuation-in-part of U.S. patent application Ser. No. 11/368,993 filed on Mar. 6, 2006 which claims the benefit under 35 USC §119(e) of U.S. Provisional Patent Application No. 60/659,771, filed Mar. 9, 2005.

BACKGROUND OF THE INVENTION

Some humans are believed to collapse part of their upper airway as they inspire during sleep causing increased resistance to airflow resulting in disruption of physiologic sleep.

Obstructive Sleep Apnea (OSA) is the term applied to this phenomenon, and it is diagnosed using electroencephalography (EEG), electro-oculography (EOG), electromyography (EMG), electrocardiography (ECG), and pulse oximetry (POX)—all well-established diagnostic tools. Breathing effort is measured as expansion of the chest and abdomen by recording the stretch of belts fitted to subjects during the study. Airflow is measured at the nose and mouth by a variety of sensors. Measurements of airflow and respiratory effort are central to the understanding of respiratory dynamics of sleep, yet these measurements are the least reliable of those available.

Inspiration in a healthy adult human creates a trans-thoracic pressure gradient of about 10 cm water by changing the position of the diaphragm and chest wall, thus expanding the chest volume and reducing intra-thoracic air pressure relative to ambient atmospheric pressure. The reduced intra-thoracic pressure causes air to flow into the lungs to equilibrate the pressure. At the same time, airway resistance in the lungs is decreasing because the lung is expanding. The inspiratory airflow in the trachea is less than about 0.5 L/sec during sleep, and the pressure gradient is dissipated linearly over about 15 cm of the trachea. As used herein, the term "healthy adult human" is a person who presents an absence of any respiratory failure, i.e. who does not have any clinically significant breathing abnormalities, such as emphysema, asthma, bronchiectasis, chronic bronchitis, and the like or is a person who is massively obese, or has unusual body habitus or has anatomical craniofacial abnormalities, or has had a stroke with bulbar palsy, or has trauma, or any other pathologies that create high, fixed upper airway resistance during sleep.

In a person afflicted with sleep apnea, in contrast, airway resistance increases during inspiration because of a presumed obstruction at the level of the hypo-pharynx (OSA). The trans-thoracic pressure gradient thus created is greater (as much as minus 40 cm water has been measured with an esophageal catheter during polysomnography) as the diaphragm and chest wall muscles contract in an attempt to overcome the increased airway resistance and maintain air flow. There is a theoretical point at which the trans-thoracic pressure gradient will be insufficient to overcome rising airway resistance. At this point, airflow will stop even in the absence of anatomic obstruction.

The act of breathing involves a variable number of inspirations per unit of time (respiratory rate) and a variable volume of air taken into the lungs with each breath (tidal volume). The product of these two is termed the 'minute ventilation.' The minute ventilation, or $V_E$, is the amount of inspired air per minute, and is controlled by the amount of dissolved carbon dioxide in the blood. Carbon dioxide ($CO_2$) is a product of combustion of hydrocarbons and is expired from the body in its gaseous form via the lungs. A rising level of dissolved carbon dioxide in the blood causes an increase in minute ventilation sufficient to return the level to normal (40 mmHg). Conversely, a falling level of dissolved carbon dioxide in the blood causes a decrease in minute ventilation sufficient to return the level to normal (40 mmHg). Each person has his/her individual "normal" blood $CO_2$ level which, for adult humans in health, is in a range of about 38 to about 42 mm Hg, wherein mm Hg is the partial pressure of $CO_2$ ($pCO_2$) in a blood sample. During the wakeful state, adjustments in response to rising and falling carbon dioxide levels are made quickly without conscious awareness.

Another form of apnea has been termed 'central sleep apnea (CSA).' It has been distinguished from OSA by the absence of apparent respiratory effort. When respiratory effort stops, minute ventilation falls to zero and carbon dioxide begins to accumulate in the blood and cerebrospinal fluid. When the $CO_2$ level exceeds 40 mmHg, inspiration begins again, and this generally causes disturbance of sleep. If, during sleep, the carbon dioxide levels fall low enough, true apnea (TA) will occur. The blood carbon dioxide level during OSA is not known with certainty. Even though respiratory effort is seen and measured in OSA, minute ventilation is presumed to be inadequate (hypoventilation) to maintain normal levels of carbon dioxide in the blood. If that were the case, carbon dioxide would accumulate in the blood and cerebrospinal fluid. During normal, awake respiration (ventilation), changes in blood carbon dioxide are rapidly corrected, but correction is slower in the cerebrospinal fluid. Carbon dioxide is freely diffusible throughout the body, but bicarbonate is transferred slowly across the blood-brain barrier. Bicarbonate neutralizes carbon dioxide that is dissolved in water (carbonic acid) and helps to adjust variations in dissolved carbon dioxide. With slower flux of bicarbonate in the cerebrospinal fluid, corrections in carbon dioxide levels will be slower and synchrony of blood chemistry and breathing dynamics will be impaired.

At sleep onset in health, minute ventilation decreases and arterial carbon dioxide accumulates establishing new parameters for adequacy of ventilation. This means that, during sleep, higher levels of carbon dioxide are necessary to stimulate breathing than during wakefulness. Without conscious awareness, hypoventilation is less discernible and carbon dioxide levels continue to increase. When this happens, an arousal occurs that is defined by convention as an increase in frequency and decrease in amplitude of the EEG. Arousals occur at the end of both 'Central' and 'Obstructive' apneas and appear, behaviorally, to be signs of respiratory distress. They indicate a switch from autonomic parasympathetic to autonomic sympathetic-nervous-system control caused by the release of stimulatory biochemicals called cathecholamines into the blood causing disruption of physiologic sleep and most of the behaviors seen with sleep-disordered breathing.

The Hering-Breuer reflex, is a vagal afferent (sensory) and efferent (motor) loop that responds to increasing chest wall tension and serves to stop and start inspiration. When chest wall tension is minimal (end expiration), vagal afferents fire at minimal frequency. At maximal chest wall tension (end inspiration), vagal afferents fire at maximal frequency. The respiratory center in the brain ends inspiration in response to this high frequency and expiration occurs passively. During 'apnea' with high trans-thoracic pressure gradients, the Hering-Breuer reflex is firing maximally.

Thus, the level of carbon dioxide in the blood determines the rate of respiration and the Hering-Breuer reflex determines the depth. Even though the respiratory effort in OSA appears diminished in 'apnea' periods, the trans-thoracic pressure gradient is quite high to match the high airway resistance. Only the resultant airflow is low (hypopnea) or zero (apnea). The damping of the waveform signal of the respiratory effort channels (chest and abdomen) only reflect decreased excursion, not effort. Therefore, the Hering-Breuer reflex is probably functioning normally and the ventilatory response to carbon dioxide is probably normal in both CSA and OSA.

The variable response time to 'apnea' (10 to 90 seconds) probably reflects the individual's rate of carbon dioxide accumulation and thus may indirectly reflect the amount of true airflow. For example, a subject who is 'apneic' for an extended period of time is probably breathing more effectively than one who is 'apneic' for a shorter period of time. Because of the poor technical quality of airflow and respiratory effort measurements, 'apnea' and 'hypopnea' are largely subjective terms. It may be more accurate to describe OSA as hypoventilation (hypercarbia) during sleep.

Arousals can also occur in the absence of a detectable respiratory event. Less is known about these kinds of arousals, but they may be due to changes in inspiratory air flow that are not detected by available technology. It is likely that all arousals are due to hypercarbia.

OSA is most commonly treated by changing from negative pressure ventilation (increased chest volume, decreased intra-thoracic pressure) to positive pressure ventilation (increased chest volume, increased intra-thoracic pressure). Compressed air is applied at the nose via a tight-fitting mask. The native respiratory rate remains intact, but the ambient air pressure is supra-atmospheric throughout inspiration and expiration. This has been termed Continuous Positive Airway Pressure (CPAP). The same pressure differential is ostensibly created in both forms of ventilation, about 10 cm water, but positive pressure seems to maintain airflow against elevated ambient inspiratory resistance better than negative pressure. Put another way, when mean air pressure above and below the putative obstruction is supra-atmospheric, flow is maintained against elevated inspiratory resistance. But, when air pressure above the putative obstruction is atmospheric but sub-atmospheric below the obstruction, flow is reduced or stopped. In fact, for normal ventilation to be perpetuated, there must be some negative pressure created. Thus, in CPAP administration, the intra-thoracic pressure still falls prior to inspiration and thus creates airflow, but the value around which the sinusoid waveform of ventilation varies is supra-atmospheric during CPAP administration.

Positive pressure also unloads the inspiratory respiratory muscles (diaphragm and chest wall muscles). In patients with chronic respiratory failure, the work of breathing must be quite high to overcome the lowered mechanical advantage and architectural changes of chronic lung disease. Positive pressure ventilation is thought to "rest" these muscles during hours of sleep. This benefit seems unrelated to OSA.

"Tracheotomy" refers to creating a passage between the outside of a patient's body and the inside of his/her windpipe or trachea. There is very little tissue between the skin and the trachea and few blood vessels and nerves at a point low in the front of the neck. An opening can be made safely at this location of the neck, and such procedures have been performed since very early in the history of medicine. "Tracheostomy" refers to creating a useful conduit out of the above referenced opening by inserting a metal or plastic device to maintain the opening and to permit the connection of other devices, such as a mechanical ventilator. Surgical tracheotomy is also an effective empirical treatment for OSA, but it was not developed for that purpose.

Tracheotomy and tracheostomy were developed for critically-ill, hospitalized patients who require mechanical ventilation for prolonged periods of time, such as more than a week. Tracheostomy appliances were designed to replace the use of endotracheal tubes inserted through the nose or mouth of the patient since long-term use of endotracheal tubes can cause unacceptable trauma to the airway and prevents the patient from eating and talking. Typically, the size of tracheostomy openings has been relatively large to permit suctioning and connections to ventilator tubing.

The surgical techniques, devices and management of tracheotomy are applied to patients with profound respiratory failure who require mechanically-assisted ventilation. Tracheotomy provides access for this ventilation. Surgical tracheotomy is also used as an alternate airway when trauma or disease has deprived a patient of the normal upper airway structures. In that case, tracheotomy may be used with or without mechanically-assisted ventilation.

Tracheostomy has been used to treat Obstructive Sleep Apnea Syndrome. In fact, it is the most effective treatment of this disorder. As discussed, supra, Obstructive Sleep Apnea Syndrome occurs when the throat or pharynx increases resistance to air inflow to the trachea during sleep. The location of the anatomical structure causing the resistance is well above the trachea. Thus, an opening created in the trachea permits air to enter the lungs in the event the above referenced resistance occurs in the throat or pharynx.

Examples of tracheostomy appliances are disclosed, for instance, in U.S. Pat. Nos. 5,464,011 issued to Bridge; 4,538,607 issued to Saul; 4,582,058 issued to Depel et al.; 6,193,751 issued to Singer; 4,877,025 issued to Hanson; 3,137,299 issued to Tabor; 3,263,684 issued to Bolton; 4,759,356 issued to Muir; 5,048,518 issued to Eliachar et al.; 5,259,378 issued to Huchon et al.; 5,392,775 issued to Adkins, Jr. et al.; 5,505,198 issued to Siebens et al.; 6,189,534 B1 issued to Zowtiak et al.; and 6,588,428 B2 issued to Shikani et al., and U.S. Patent Application Publication No. 2004/0123868 A1 of Rutter.

While the above referenced tracheostomy appliances may function in an acceptable manner for their intended purposes, there is a need for tracheostomy appliances and methods specifically designed to treat Sleep Apnea Syndromes in adult patients in health.

BRIEF SUMMARY OF THE INVENTION

More specifically, in one embodiment of the present invention, useful in treating apneic patients in health, a small caliber catheter is emplaced surgically trans-tracheally for equalizing intra-tracheal pressure relative to ambient pressure under certain conditions of inspiration by permitting very limited air inflow. This miniature version functions to prevent an undersirable increase in $CO_2$ level which would otherwise cause arousal from sleep. It presents a minimal adverse affect on patient appearance.

In another embodiment of the present invention a tracheostomy appliance is provided by a cannula having an airway between opposite ends and a valve within the cannula for closing the airway when airway resistance across the valve is less than a predetermined value and for opening the airway when airway resistance across the valve exceeds the predetermined value. The valve only opens when the throat or pharynx of its wearer collapses during sleep, and the airway is sized to permit passage of somewhat greater limited airflow than the first embodiment, when open.

According to another aspect of the present invention, methods are provided for treating either Central or Obstructive sleep apnea syndromes using the above referenced devices.

BRIEF DESCRIPTION OF THE DRAWINGS

The foregoing and other objects, features and advantages of the present invention should become apparent from the following description when taken in conjunction with the accompanying drawings, in which:

FIG. 2 is an enlarged side view of the miniature embodiment;

FIG. 3 is an proximal end view of the miniature embodiment with cap removed;

FIGS. 4A and 4B are perspective views of a valve mechanism for the miniature embodiment;

FIGS. 5A, 5B and 5C are perspective views of a trocar used to implant the miniature embodiment;

FIG. 9 is an exploded, somewhat schematic, elevational view of an embodiment similar to the embodiment of FIG. 7;

DETAILED DESCRIPTION OF THE INVENTION

Figure 1:
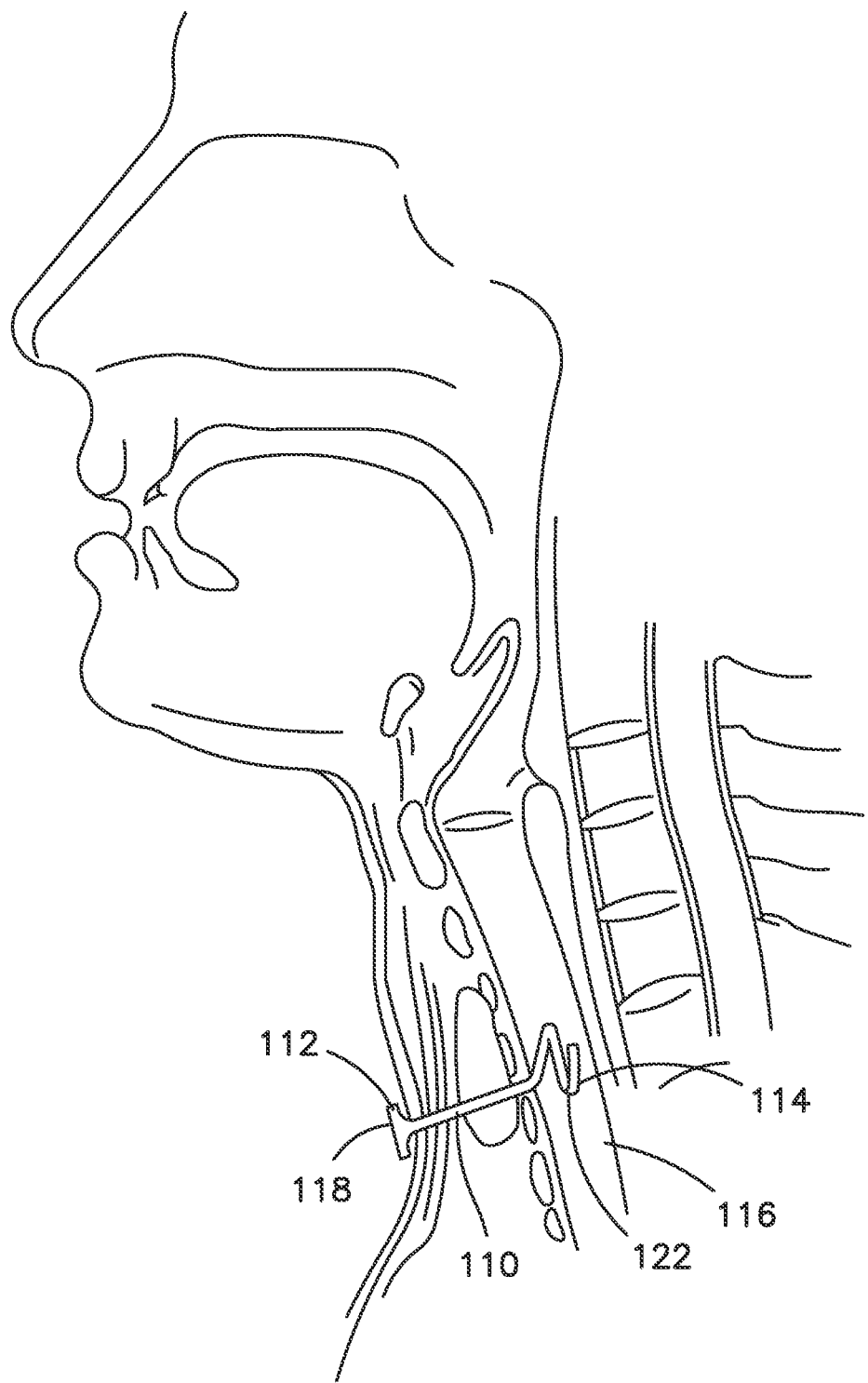
FIG. 1 is a vertical sectional view of a miniature embodiment of the invention shown implanted in a patient's trachea for treating in health apneic patients.

With the Background of the Invention in mind, and incorporated by reference herein, and with reference to the Drawings, the miniature embodiment of FIGS. 1-3, is described in conjunction with a method of treating an adult patient in health for sleep apnea.

Referring to FIG. 1, the method comprises the step of implanting in a tracheotomy, an appliance, such as a catheter 110, having a vent 112 with at least one distal port 114 communicating with the interior of the patient's trachea 116 and a proximal port 118. (As used herein, proximal is nearer to the implanting surgeon, and distal further from the implanting surgeon.) The distal port 114 is for the purpose of sensing intra-tracheal pressure, and the proximal port 118 is for sensing ambient atmospheric air pressure which, at sea level under standard conditions is 1000 mm Hg. In the illustrated embodiment, the vent 112 provides a small continuous flow path between the proximal and distal ports, 118 and 114.

A removable closure cap 120 is provided for releasable attachment adjacent the proximal end 118 of the catheter 110. The cap 120 may be applied diurnally for precluding foreign matter from entering the trachea 116 through the vent during normal diurnal activities. When preparing for nocturnal sleep, the patient removes the cap 120.

With the cap 120 removed, the distal port 114 communicates directly with the proximal port 118. Normally during inhalation, intra-tracheal air pressure is lower than ambient air pressure due to the "suction" created in the lungs. However, during a period of incipient apnea in an apneic patient, there is an abnormal decrease in intra-tracheal pressure. In the present invention, this abnormal decrease in pressure causes sufficient volume of air to flow through the catheter 110 and substantially equalizes intra-tracheal pressure with ambient pressure. The volume of air is very small, but is sufficient to attenuate incipiently a proclivity for $CO_2$ to increase to an undersirable level that otherwise would increase and cause arousal of the patient from sleep.

By way of example, and not by way of limitation, a sufficient volume of air should limit the increase in blood carbon dioxide to less than about twenty-five (25%) of the patient's normal level of blood carbon dioxide. Preferably, the magnitude of increase in blood carbon dioxide level is less than about 10 mm Hg.

Such limitations on increase in carbon dioxide levels should be obtainable with a total volume of air flow into the trachea of about 0.05 liters. Preferably, the above volume is flowed at an average rate of less than about 8 liters per minute, and more preferably, the volume is flowed at less than about four (4) liters per minute for less than about one (1) second. The air is preferably flowed continually between the proximal port 118 and the distal port 114 within the catheter 110.

A desirable catheter 110 for practicing the above method has a circular interior cross-section with an inside diameter, or caliber, of less than about 4 mm, or size 9 French. The catheter 110 carries an anti-withdrawal anchor for engaging the inside wall of the trachea 116, and is preferably remotely deployable from the proximal end portion of the catheter 110. As illustrated in FIGS. 5A-5C, one form of remotely deployable anchor has a helical arcuate shape 122 adjacent the distal port 114. The arcuate shape 122 is straightened by means of an axially displaceable trocar 124 removably located inside the catheter 110. During insertion, the trocar 124 maintains the catheter in an erect configuration (see FIG. 5A) until the helical anchor 122 is properly located within the trachea 116, and the trocar 124 is then withdrawn axially outward (see FIGS. 5B and 5C) to complete the emplacement.

In the embodiment of FIGS. 1 and 2, the catheter 110 has a relatively short length "L" which can be provided in various lengths or cut to size during it's implanting. A desirable length "L" is about 5 cm.

Figure 6A:
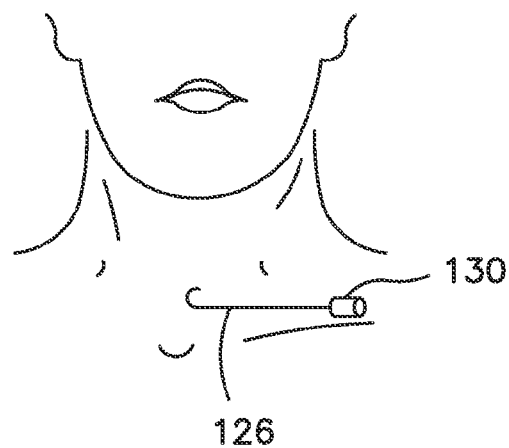
FIGS. 6A and 6B are views of a miniature embodiment implanted subcutaneously and extending along the patient's clavicle.
Figure 6B:
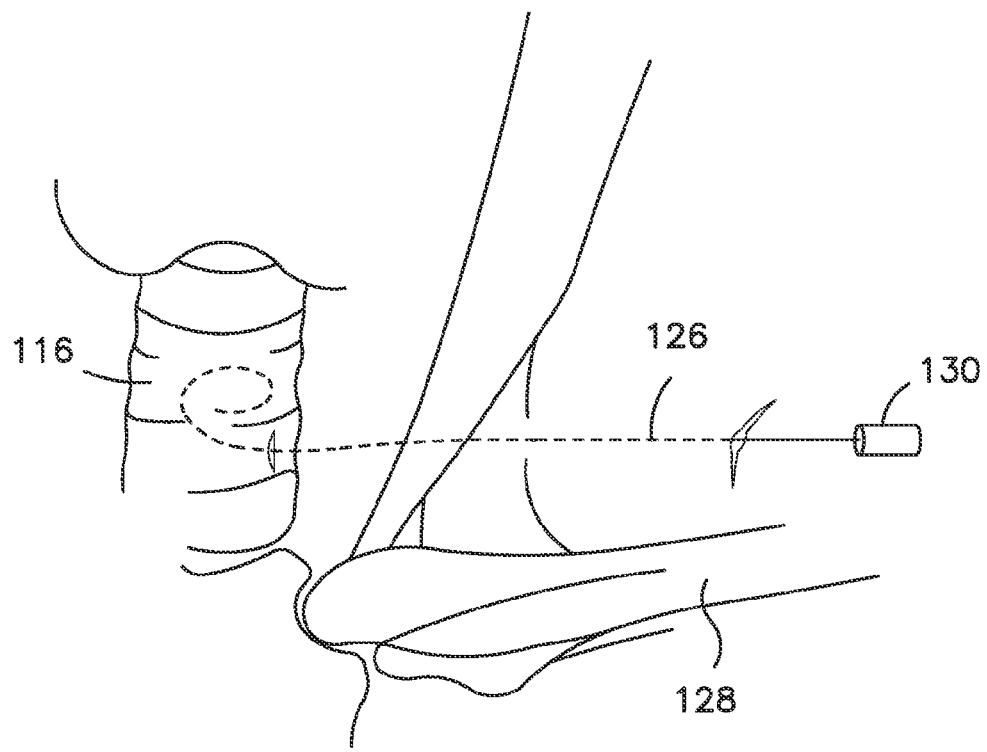

In situations where cosmesis is important to the patient, an elongate catheter 126 may be inserted laterally into the trachea and extended sub-cutaneously along the clavicle 128 to locate the proximal port 130 to one side of the patient's neck in a region normally covered by clothing. See FIGS. 6A and 6B.

A check valve 132 may be mounted adjacent the proximal end 118 of the catheter 110 disposed to open toward the trachea 116 in response to a sustained increase in negative pressure in the trachea 116 to afford air inflow. As an example, FIGS. 4A and 4B show a valve mechanism 132 including a perforated plate 134 and a flexible disk 136 overlying the perforations 138 of the perforated plate. The flexible disk 136 is secured at its center by a small rivet 140, as shown in FIGS. 2 and 4A. The rivet 140 holds the disk centrally and enables its outer peripheral margin to flex and lift off the perforations, as shown in FIG. 4B. The normal closed condition of the valve 132 is illustrated in FIG. 4A and the open condition of the valve is illustrated in FIG. 4B. The arrows in FIGS. 4A and 4B show airflow.

Figure 7:
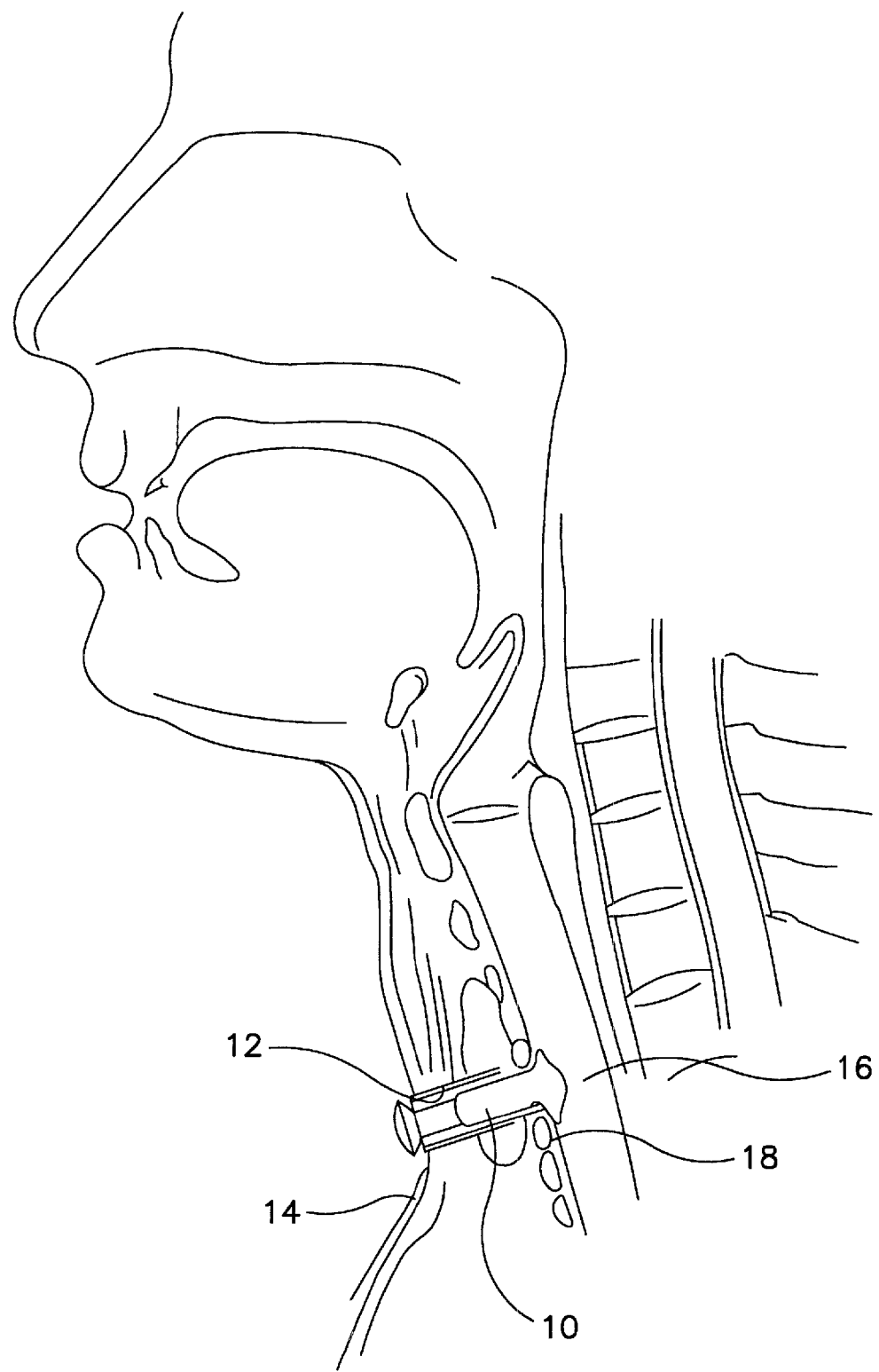
FIG. 7 is a view similar to FIG. 1, but illustrating another embodiment particularly suited for treating other types of apneic patients.

Referring to FIGS. 7-11, the present invention also provides a valved tracheostomy appliance particularly suited for patients for whom the miniature version of FIG. 1 may not be indicated, such as patients who may not be in health or who may have use in treating Obstructive Sleep Apnea Syndrome. As illustrated in FIG. 7, the tracheostomy appliance 10 is inserted in a tracheostomy opening, or incision, 12 formed at a location low on the front of a patient's neck. The appliance 10 provides an airway that extends from the outer surface 14 of the patients skin to an airway 16 within the trachea 18.

A very small opening 12 is provided, such as less than about 1.0 centimeter in diameter. With an adult in health, the normal respiratory rate at rest is 12-16 times per minute, or about one breath every 4 to 5 seconds, and the volume of air per breath is about 500 cc. Thus, at a rate of about 100-125 cc per second, it takes about 4 to 5 seconds to inhale 500 cc of air. Allowing a safety factor of two would bring the rate to about 250 cc per second. Accordingly, a small opening of about 1.0 centimeter in diameter should allow passage of the above stated amount of air.

For the treatment of Obstructive Sleep Apnea Syndrome, the opening 12 is required only when the upper airway becomes obstructed during sleep. It is not required when the patient is awake, such as during the day. Preferably, the opening 12 is capable of being closed when the patient is awake to preserve the usual anatomy and physiology of the patient's airway and to greatly lower the patient's exposure to infection.

The appliance 10 according to this embodiment of the present invention has a normally-closed valve 20 that remains closed during regular breathing regardless of whether the patient is sitting, standing or lying. This may be accomplished, for instance, by weighting the valve 20 and by proper positioning of the valve 20 relative to the patient. For example, the valve 20 may be constructed as a thin disk 22 that is free to rotate, or pivot, on a small-caliber rod, or wire, 24 located inside a cylindrical valve housing 26. The disk 22 may be weighted and positioned so that it falls closed when the patient is standing, sitting or lying supine. Preferably, the center of gravity of the disk 22 is located below the point of suspension of the disk 22 on the rod, or wire, 24.

The valve 20 is designed to open only when a certain value of airway resistance is experienced by the patient. For example, the valve 20 may be designed to open when airway resistance is about 10 cm $H_2O$, which relates to a normal pressure gradient for breathing during sleep based on esophageal manometry studies. Of course, the valve 20 can be set, or designed, to open for any value of airway resistance deemed desirable.

Figure 8:
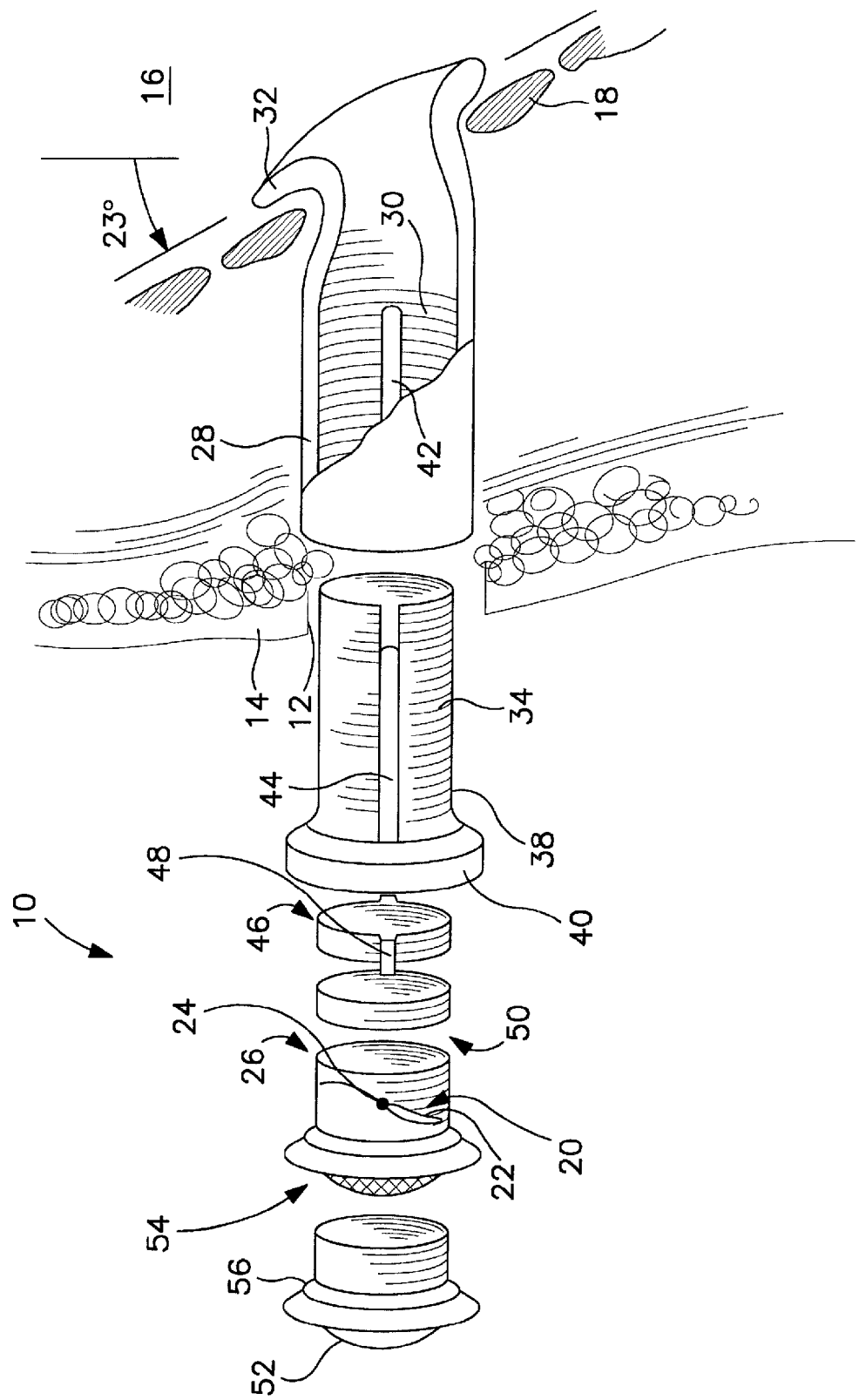
FIG. 8 is an exploded, somewhat schematic, perspective view of the embodiment illustrated in FIG. 7.
Figure 10:
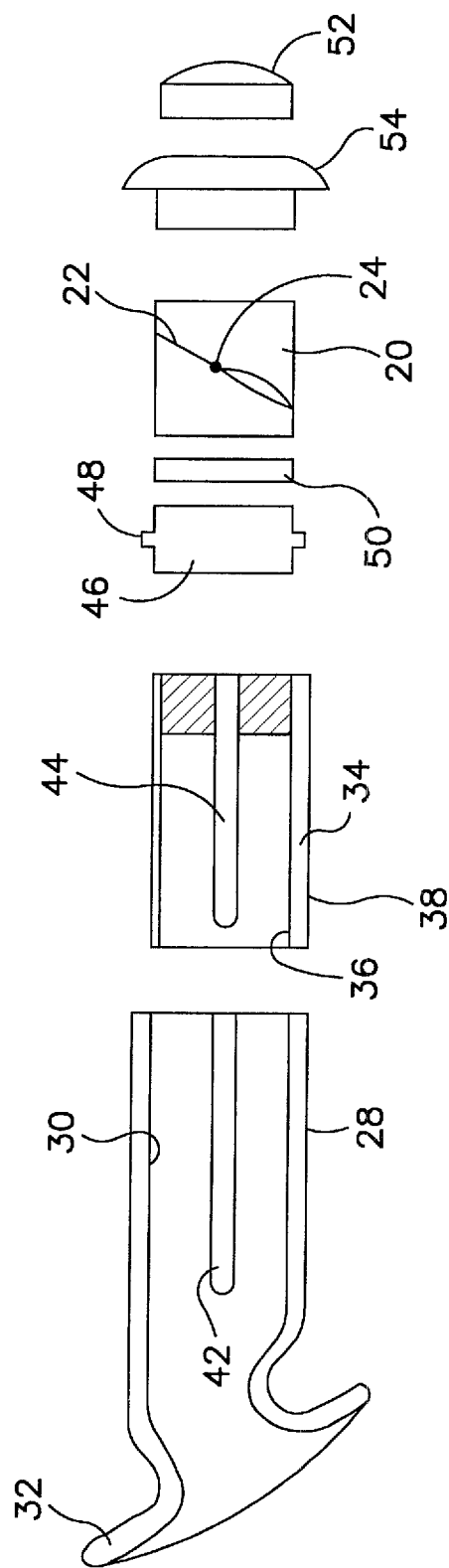
FIG. 10 is a partial cross-sectional view of the embodiment of FIG. 9.

The appliance 10 according to the embodiments illustrated in FIG. 8-10 is preferably made of several substantially cylindrical pieces that assemble telescopically. A first cannula, or cylinder, 28 is approximately 3 cm long and 1.5 cm in diameter, has fine threads 30 on an inner side thereof, and has a smooth flange 32 at one end thereof. A second smaller caliber cylinder, or cannula, 34 of similar dimensions has fine threads 36 and 38 on inner and outer sides thereof (see FIG. 10 for threads 36) and may (FIG. 8) or may not (FIGS. 9 and 10) have a smooth flange 40 at one end thereof. The larger cannula 28 is inserted into the small percutaneous tracheotomy incision 12 such that the flange 32 gains purchase on the inside of the trachea 18. The smaller cannula 34 is then screwed into the larger cannula 28 via mating threads 38 and 30 until the flange 40 of the smaller cannula 34 engages the patient's skin surrounding the incision 12. Thus, the appliance 10 is anchored, or secured, it in place in the fashion of a grommet.

Preferably, a pair of diametrically-opposed longitudinal channels 42 and 44 extend in the walls of both cannulas, 28 and 34. The channels 44 in the smaller cannula 34 extend only part way along the length of the cannula 34 and extend through the full thickness of the walls of cannula 34 (ie., providing openings in the walls of the cannula 34). The channels 42 in the larger cannula 28 are of a depth of about half the thickness of the walls of the cannula 28 and may extend approximately the full length of the cannula 28, if desired. The channels 42 and 44 can be aligned when the two cannulas 28 and 34 are screwed together and form part of a locking mechanism. A non-threaded ring 46 which is slightly smaller in caliber than the inner diameter of cannula 34 has a pair of diametrically opposed protrusions 48 that slide in the channels 42 and 44. Thus, by aligning the channels 42 and 44 and by sliding the ring 46 into place within the cannulas 28 and 34, the cannulas 28 and 34 are locked and prevented from becoming unintentionally unscrewed. A threaded ring, or locking nut, 50 is then screwed in place against the locking ring 46 to lock the ring 46 within the cannulas 28 and 34.

After the cannulas 28 and 34 are locked together, the valve housing 26 is installed within cannula 34. Preferably, the housing 26 is substantially cylindrical, has a length of about 10 to 15 mm, and is threaded. Thus, the valve housing 26 is screwed into place within the proximal end of the appliance 10. As stated above, a weighted valve 20 is carried by the housing 26 and remains closed whether the patient is in an erect or supine position.

By way of example, the valve 20 may include a flat disk 22 of a size necessary to substantially close the path defined by the inner diameter of the housing 26. The disk 22 should be capable of movement relative to the walls of the housing 26 and should not stick to the walls of the housing 26. The disk 22 should be mounted on a rod or wire 24 that extends within the housing 26 between diametrically-opposed apertures formed in the walls of the housing 26. The disk 22 is permitted to freely rotate on the wire or rod 24, and one half of the disk 22 is weighted. The weight, for example, could be the amount necessary to permit the valve 20 to open when a pressure gradient of about 10 cm $H_2O$ exists across the valve 20. Up to that pressure difference, the valve 20 would remain in a closed position. The minimum cross sectional area of the appliance 10 with the valve 20 in place and in the open position must allow about at least 100 ml, preferably 250 ml, of air to pass per second to safely achieve its desired purpose. A very light torsion spring may be employed in lieu of the weighted disk to provide a desired closing bias.

Preferably, the appliance 10 includes a pair of caps 52 and 54 that each screw, or snap, into the proximal end of the valve housing 26. Cap 52 is solid and domed and provides a water-tight seal for use during the day. Cap 54 is a domed mesh filter cap that is utilized during sleep to prevent foreign bodies from entering the trachea when the valve 20 is in an open position. Preferably, both caps 52 and 54 carry an "O"-ring gasket 56.

Figure 11:
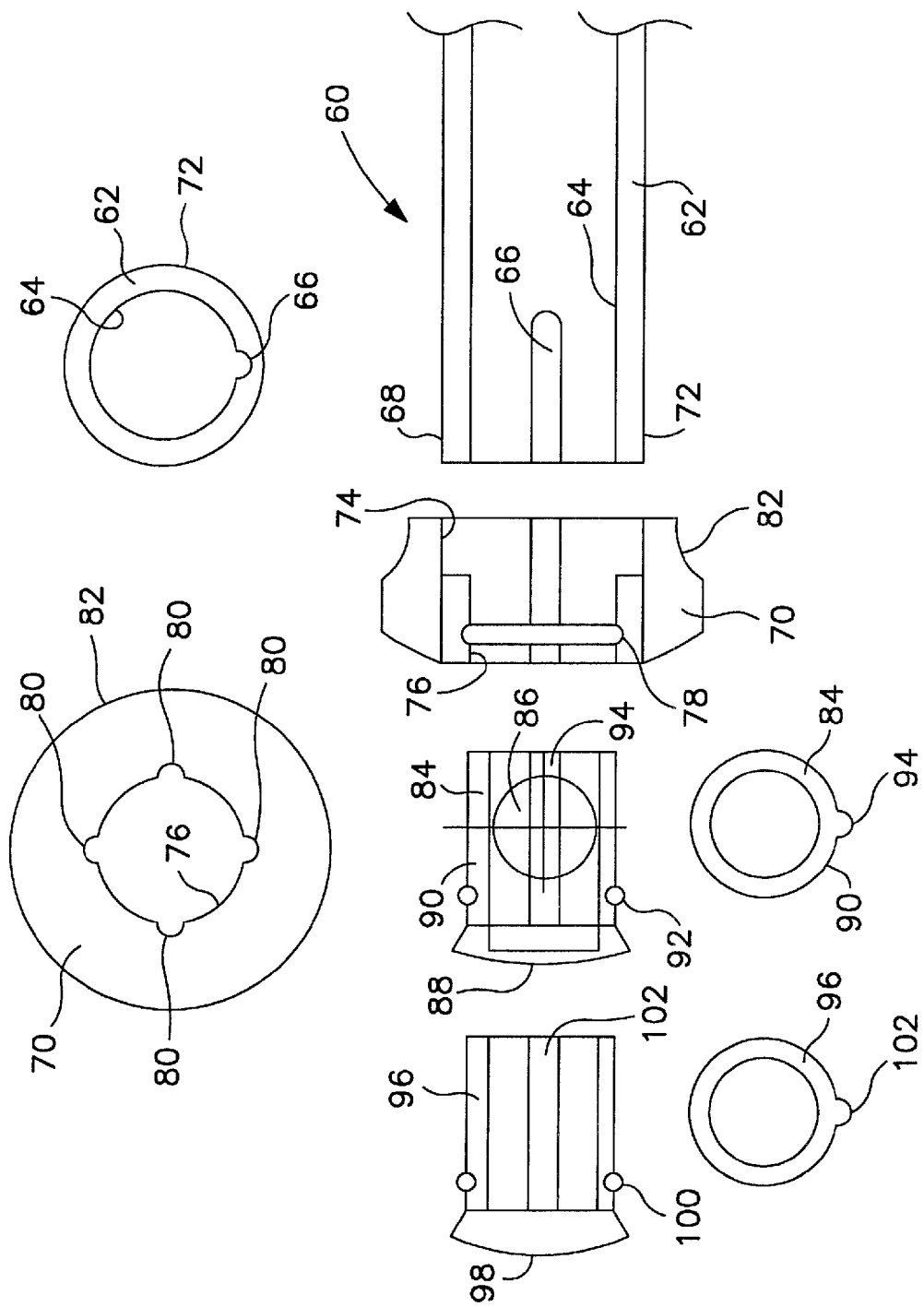
FIG. 11 is a partial exploded cross-sectional view of another alternate embodiment of the embodiment of FIG. 7.

A further alternate embodiment of a valved tracheostomy appliance 60 is illustrated in FIG. 11. The appliance includes an inner cannula 62 that is similar to the cannula 28 of appliance 10 discussed above. (A flanged distal end of the cannula 62, identical to flange 32 illustrated in FIGS. 8-10, is not shown in FIG. 11 for ease of illustration.) The inner peripheral wall 64 of cannula 62 is smooth and without threads to help maintain the sterility of the appliance after it has been placed in the patient. A longitudinally-extending groove 66, such as a rounded groove, extends on the inner peripheral wall 64 adjacent a proximal end 68 of the cannula 62.

Preferably, the inner cannula 62 is provided in a predetermined length that can be cut so that a custom fit can be provided for each patient and so that the appliance 60 can accommodate different neck sizes and length requirements. The required length of appliance 60 can be determined by a computed tomographic image of the neck before surgery.

An annular flange 70 connects to the proximal end 68 of the cannula 62 to secure the position of the inner cannula 62 in situ by acting as an outer half of a grommet-type structure. Preferably, the connection is a threaded connection between an outer peripheral wall 72 of cannula 62 and an inner annular threaded wall 74 of flange 70. The flange 70 illustrated in FIG. 11 also includes an inner wall 76 that includes a circumferential groove 78 and four longitudinally-extending grooves 80 equally spaced about wall 76. The purpose of grooves 78 and 80 are discussed below. An outer wall 82 of flange 70 is preferably flared in such a way that it prevents tissue trauma to the patient as the flange is being assembled with the cannula 62.

The appliance 60 also includes a valve housing cap 84 that houses a weighted valve 86 and that carries an outer mesh cover 88. The weighted valve 86 is substantially identical to valve 20 discussed above. An outer peripheral wall 90 of housing cap 84 has a circumferentially-extending O-ring 92 and a longitudinally-extending locking rib 94.

When the annular flange 70 is connected to the cannula 62, one of the grooves 80 of the flange 70 is aligned with the groove 66 of the cannula. The flange 70 is provided with four grooves 80 to permit groove alignment ever quarter turn of the flange 70 ensuring tight securement of the flange 70 to the cannula 62. Thereafter, the valve housing cap 84 is inserted into the annular flange 70 such that the rib 94 of the valve housing cap 84 is received within one of the grooves 80 of the annular flange 70 and the groove 66 of the cannula 62. Placement of rib 94 in the grooves locks the cannula 62, annular flange 70 and valve housing cap 84 in proper alignment, which in turn ensures that the valve 86 is properly positioned within the patient's neck.

The appliance 60 can also be provided with a solid cap 96 that can be inserted into annular flange 70 when the valve housing cap 84 is removed. The cap 96 is similar in structure to valve housing cap 84, except that it does not include a valve 86 and has a solid outer cover 98 instead of a mesh cover. Thus, the cap 84 includes an O-ring 100 and locking rib 102.

As discussed above in detail, the appliance 60 has a simplified design requiring the assembly of only three parts including a cap, 84 or 96, annular flange 70, and inner cannula 62. Preferably, the appliance 60 is made of lightweight medical grade, inert plastic material, and the caps 84 and 96 are easily removable and interchangeable by the patient or caregiver.

The parts of appliances 10 and 60 are easily manipulated by the patient and the surgeon. The appliance, 10 or 60, is surgically implanted in the neck of the patient. Sterility is maintained by using a small ultrasonic cleaning device and sterile soaking solutions as part of a system similar to that used in contact lenses. Other than that, maintenance and cleaning of the appliances 10 and 60 can be accomplished by health-care professionals as part of routine scheduled follow-up checks.

The valved tracheostomy appliance according to the present invention is appropriate for treatment of OSA whether scoring high or low in terms of apnea events as a first choice instead of as a last choice as currently provided with known devices. It is particularly useful in patients unwilling or unable to tolerate nasal CPAP, the current treatment of choice. Use of the appliances of the present invention should be less risky, more comfortable, better tolerated and more effective than any other surgical procedure currently offered. The procedure for implanting the appliance can be done quickly and effectively without the need of operating room facilities and/or general anesthesia.

This embodiment may also be used to treat sleep apnea patients in health by substituting, for the valve, an orifice plate having a hole with a caliber of about the same size as described heretofore in connection with the embodiment of FIGS. 1-3. This would enable the appliances 10 or 60 to be used in a patient whose OSA may improve so that a valved device is no longer required.

While preferred tracheostomy appliances have been described in detail, various modifications, alterations, and changes may be made without departing from the spirit and scope of the appliance according to the present invention as defined in the appended claims.

The invention claimed is:

1. A method of treating a human patient having sleep apnea, comprising the steps of:
    implanting in the patient's trachea an appliance consisting essentially of a catheter having an inside diameter of less than about 4 mm. for providing a vent with a distal port communicating with the interior of the trachea for sensing intra-tracheal pressure and a proximal port for sensing ambient pressure, and an anchor adjacent said distal port for engagement with the interior of the trachea,
    deploying said anchor into operative engagement with the interior of the trachea from a remote location outside of said trachea;
    disposing a closure operable manually adjacent said proximal port between a closed position completely blocking air flow into the vent and an open position for admitting air flow into the vent;
    causing said closure to be disposed in its open position before said patient embarks on a desired sleep phase for permitting said distal port to sense an abnormal decrease in intra-tracheal pressure relative to said ambient pressure during said desired sleep phase of the human patient, and
    in response to said abnormal decrease in intra-tracheal pressure, enabling only a sufficient volume of air at ambient pressure to flow through said distal port effective to reduce said abnormal decrease in pressure between the interior of the trachea and ambient for limiting an increase in carbon dioxide accumulation to less than about 25 percent of the patient's normal level operable to effect arousal from desired sleep.

2. A method according to claim 1, wherein the magnitude of said increase of carbon dioxide level is less than about 10 mm Hg.

3. A method according to claim 2, wherein said sufficient volume of air flow is less than about 0.05 liters.

4. A method according to claim 1, wherein said sufficient volume of air is flowed at an average rate of less than about 8 liters per minute through said vent.

5. A method according to claim 4, wherein said sufficient volume of air is flowed at an average rate of less than about 4 liters per minute for less than about one second.

6. A method according to claim 1, wherein said vent provides said sufficient volume of air between said distal port and said proximal port.

7. A method according to claim 1, wherein said remotely deployable anchor includes a resiliently deformable normally arcuate shape on said vent adjacent said distal port for operative engagement with the interior of the trachea, and including an actuator removably slidable axially in said vent for effecting insertion and withdrawal of said anchor.

8. A method according to claim 1, wherein said appliance carries a normally-closed check valve in said vent operable to open in response to a transient sustained pressure difference between ambient pressure and said abnormal pressure in said trachea.

9. A method according to claim 1, wherein said appliance vent has a predetermined length between said proximal port and said distal port, and wherein substantially the entire length is disposed subcutaneously in said patient after said implanting step.

10. A device for implantation in a human patient's trachea for treating sleep apnea, comprising:
a catheter having an inside diameter of less than about 4 mm. providing a vent with a distal port and a proximal port, said distal port, when implanted, being disposed inside the trachea for communicating with the interior of the trachea for sensing intra-tracheal pressure and said proximal port, when implanted, being disposed outside the trachea for sensing ambient pressure;
a remotely deployable anchor carried by said catheter adjacent said distal port for operative engagement with the interior of the trachea;
a closure disposed adjacent said proximal port and being selectively manually operable between a closed position completely blocking air flow into said proximal port and an open position affording air flow into said proximal port; and
an actuator extending along said catheter for deploying said anchor against the inside of said trachea from a remote location outside said trachea;
whereby, in response to an abnormal decrease in intra-tracheal pressure, said appliance enables only a sufficient volume of air at ambient pressure to flow through said distal port effective to reduce said abnormal decrease in pressure between the interior of the trachea and ambient for incipiently attenuating an undesirable increase in carbon dioxide accumulation normally operable to effect arousal of the patient from sleep.

11. A device according to claim 10, wherein said vent provides the sufficient volume of air between said distal port and said proximal port.

12. A device according to claim 10, wherein said remotely deployable anchor includes a resiliently deformable normally arcuate shape on said vent adjacent said distal port for operative engagement with the interior of the trachea, and including an actuator removably slidable axially in said vent for effecting insertion and withdrawal of said anchor.

13. A device according to claim 10, wherein said appliance carries a normally-closed check valve in said vent operable to open in response to a transient sustained pressure difference between ambient pressure and abnormal pressure in said trachea.

14. A device according to claim 10, wherein said appliance vent has a predetermined length between said proximal port and said distal port, and wherein substantially the entire length is adapted to be disposed subcutaneously in said patient.

15. A device for implantation in a human patient's trachea for treating sleep apnea, comprising:
a flexible catheter having an inside diameter of less than about 4 mm. providing a vent with a distal port and a proximal port, said distal port, when implanted, being disposed inside the trachea for communicating with the interior of the trachea for sensing intra-tracheal pressure and said proximal port, when implanted, being disposed outside the trachea for sensing ambient pressure;
said catheter having a normally-arcuate end portion providing a remotely deployable anchor carried adjacent said distal port for operative engagement with the interior of the trachea;
a closure disposed adjacent said proximal port and being selectively manually operable between a closed position completely blocking air flow into said proximal port and an open position affording air flow into said proximal port; and
an actuator extending along said catheter for deploying said anchor against the inside of said trachea from a remote location outside said trachea;
said actuator being axially telescopically slidable within said catheter for straightening its arcuate and portion during implantation thereof and being removable upon implantation and deployment of said anchor,
said catheter being operable in response to an abnormal decrease in intra-tracheal pressure to cause less than about 0.05 liters of air at ambient pressure to flow through said distal port for limiting any increase in carbon dioxide accumulation in the patient to less than about 10 mm Hg.

* * * * *